United States Patent
Spannagel et al.

(10) Patent No.: US 8,046,176 B2
(45) Date of Patent: Oct. 25, 2011

(54) DEVICE AND METHOD FOR DETERMINING MATERIAL MOISTURE BY THERMOGRAVIMETRY

(75) Inventors: Wilfried Spannagel, Goettingen (DE); Sven Hollstein, Hannover (DE)

(73) Assignee: Sartorius Weighing Technology GmbH, Goettingen (DE)

( * ) Notice: Subject to any disclaimer, the term of this patent is extended or adjusted under 35 U.S.C. 154(b) by 0 days.

(21) Appl. No.: 12/792,491

(22) Filed: Jun. 2, 2010

(65) Prior Publication Data
US 2010/0241364 A1 Sep. 23, 2010

Related U.S. Application Data

(63) Continuation of application No. PCT/EP2008/008604, filed on Oct. 11, 2008.

(30) Foreign Application Priority Data

Dec. 3, 2007 (DE) .......................... 10 2007 058 390

(51) Int. Cl.
*G01N 25/00* (2006.01)
(52) U.S. Cl. ........................................................ 702/24
(58) Field of Classification Search .................... 702/24; 374/14; 34/259
See application file for complete search history.

(56) References Cited

U.S. PATENT DOCUMENTS

| 4,485,284 | A | * | 11/1984 | Pakulis | .......................... 219/705 |
| 6,092,924 | A | * | 7/2000 | Scalese et al. | ................... 374/14 |
| 2002/0035792 | A1 | * | 3/2002 | Scalese et al. | ................... 34/259 |
| 2007/0199370 | A1 | | 8/2007 | Diedrich et al. | |

FOREIGN PATENT DOCUMENTS

| EP | 1318699 A2 | 6/2003 |
| GB | 2202054 A | 9/1988 |
| WO | 99/61878 A2 | 12/1999 |
| WO | 00/14552 A1 | 3/2000 |
| WO | 00/16067 A1 | 3/2000 |
| WO | 2006/048080 A1 | 5/2006 |

* cited by examiner

*Primary Examiner* — Cindy Hien-Dieu Khuu
(74) *Attorney, Agent, or Firm* — Sughrue Mion, PLLC

(57) ABSTRACT

A device and a method for determining material moisture by thermogravimetry. Included in the device are: a test chamber (2) delimited by a chamber cover (8); a microwave field that can be generated by a magnetron (5) and supplied to the test chamber by a waveguide (4); a tuning rod (22) arranged in the test chamber; a sample carrier (3) which is operatively connected to a weighing module (6) mounted upstream of the test chamber; and at least one sensor (24) arranged in the test chamber. The tuning rod is arranged centrally on the chamber cover, above the sample carrier, and the at least one sensor is arranged on the free end of the tuning rod, opposing the chamber cover.

8 Claims, 4 Drawing Sheets

DEVICE AND METHOD FOR DETERMINING MATERIAL MOISTURE BY THERMOGRAVIMETRY

This is a Continuation of International Application PCT/EP2008/008604, with an international filing date of Oct. 11, 2008, which was published under PCT Article 21(2) in German, and the complete disclosure of which is incorporated into this application by reference.

FIELD AND BACKGROUND OF THE INVENTION

The invention relates to a device for determining material moisture by thermogravimetry, comprising a test chamber that is delimited by a chamber cover, a microwave field which can be generated by a magnetron and fed via a waveguide to a test chamber, a tuning rod arranged in the test chamber, a sample carrier which is in operative connection with a weighing module mounted upstream of the test chamber, and at least one sensor arranged in the test chamber.

The invention also relates to a method for determining material moisture wherein a sample placed on a sample carrier in a test chamber has moisture removed therefrom by heating in a microwave field generated by a magnetron and fed to the test chamber via a waveguide, while being monitored by at least one sensor and the weight of the sample is determined by a weighing module before and after moisture removal and used in a computer unit to determine the material moisture.

Devices and methods for thermogravimetric material moisture determination are used in industrial laboratories, mainly in the food and drink industries and the chemical and pharmaceutical industries, but also in the cosmetics, animal feed and building material industries for thermogravimetric material moisture determination.

U.S. Pat. No. 6,247,246 B1 discloses a device for thermogravimetric material moisture determination, which comprises a cylindrical test chamber with a sample carrier in operative connection with a weighing module, onto which sample carrier the sample to be measured is placed. A microwave field generated by a magnetron can be fed to the test chamber via a waveguide to desiccate the sample. The moisture removed from the sample can be drawn off by fans via apertures in the chamber cover which end in at least one exhaust air channel. The known device has at least one microwave sensor in the chamber cover. In addition, a gas or smoke sensor and a sensor for detecting light or light flashes can be arranged in the chamber cover. In order to allow the microwave field to act effectively on the sample, two tuning rods are arranged laterally of the sample at the test chamber base, adjacent to two portals for feeding the microwaves into the test chamber.

OBJECTS AND SUMMARY OF THE INVENTION

A disadvantage of the known device, which has overall proven to be quite effective in practice, is that it is relatively difficult to detect rapidly the end of the drying process so that the sample can be weighed again. This involves an unnecessary loss of time. The use of a plurality of microwave sensors proposed in U.S. Pat. No. 6,247,246 B1 does not, in practice, lead to a shortening of the measuring process.

It is therefore an object of the present invention to improve the known device such that the thermogravimetric material moisture determination can be carried out more rapidly.

This object is achieved, according to one formulation of the invention, in that the tuning rod is arranged at the chamber cover centrally above the sample carrier and that at least one sensor is arranged at the free end of the tuning rod facing away from the chamber cover.

The tuning rod arranged centrally above the sample unexpectedly leads to a microwave field of similar quality to that with the known two tuning rods arranged laterally relative to the sample at the chamber base as special means for influencing the microwave field. The sensor arranged on the tuning rod closely above the sample also leads to a quicker result.

Effectively measuring close to the sample also means that any overloading due to overheating of the sample will be more rapidly detected, so that the device is safer overall.

According to a preferred embodiment of the invention, the sensor arranged on the tuning rod is configured as a microwave sensor or a no-contact temperature sensor, for example, an infrared sensor. A second sensor which is configured as a no-contact temperature sensor (if the sensor on the tuning rod is configured as a microwave sensor) or as a microwave sensor (if the sensor on the tuning rod is configured as a temperature sensor) is arranged in the test chamber.

According to another embodiment of the invention, in addition to the one or more sensors in the test chamber, an air moisture sensor is also arranged in the exhaust air stream in the test chamber.

The placement of different sensors which support the actual measuring process enables simultaneous measurement or monitoring of the moisture indirectly by the microwave sensor via the alteration of the microwave field in the test chamber, as well as measurement of the air moisture in the exhaust air stream by the air moisture sensor. The end of the drying process can thus be detected more rapidly and the moisture in the sample can be determined quicker and more reliably.

According to another embodiment of the invention, a temperature sensor is provided at the magnetron.

With the temperature sensor, possible overloading of the magnetron can be detected early and counteracted, for example, by a power reduction in the microwave field and/or by switching on further fans or increasing the fan power.

According to a preferred embodiment of the invention, the waveguide is fixed, and the sample carrier is rotatable about a vertical rotation axis via which said sample carrier is connected to the weighing module. Exhaust air apertures, via which an air stream generated by at least one fan can be conducted out of the test chamber to the outside, are provided in the chamber cover.

U.S. Pat. No. 6,247,246 B1 also discloses a method for rapid thermogravimetric material moisture determination. In this known method, the loss of moisture on drying a sample is determined. The sample is placed on a sample carrier in a cylindrical test chamber for drying and the weight thereof is determined. A microwave field is generated in the test chamber and the change in the microwave energy, which corresponds to the loss of fluid in the sample, is monitored by a microwave sensor. Following completion of the drying process, the weight is determined again.

A disadvantage of the known method, which has proven to be quite effective, is that it is relatively difficult to recognize the end of the drying process for the sample to be weighed again. An undesirable loss of time is unavoidable and overloading of the sample or individual components of the device can occur. It has been found that the use of a plurality of microwave sensors proposed in U.S. Pat. No. 6,247,246 B1 is not effective.

It is therefore a further object of the invention to improve the known method such that it can be carried out quicker and more reliably.

According to a further formulation of the invention, this is solved in that, in the test chamber, the microwave field is monitored by a microwave sensor and/or the temperature generated by the microwave field is monitored by a no-contact temperature sensor and, simultaneously, the exhaust air stream from the test chamber is monitored by an air moisture sensor. The monitored values thus determined are then used for controlling the material moisture determination.

Through simultaneous measurement or monitoring of the moisture indirectly via the change in the microwave field in the test chamber and the measurement of the air moisture in the exhaust air stream, the end of the drying process can be more rapidly detected and the moisture of the sample can be determined more rapidly and reliably.

According to a preferred embodiment of the invention, the temperature is also monitored at the magnetron with a temperature sensor and the monitored value thus determined is used for controlling the material moisture determination.

With the temperature sensor, possible overloading of the magnetron can be recognized early and counteracted by, for example, reducing the power of the microwave field and/or by switching on further fans or increasing the fan throughput. The power of the fans can also be controlled by sensors assigned specifically to the fans.

The heating power of the microwave field can be controlled by at least one of the sensors. Particularly when inverter technology is used, the power, and thus the heating output, of the microwave field can be controlled by the values determined by the sensors. The settings of electronic filters, measurement end detection and a measurement end value prediction can be controlled by at least one of the sensors.

BRIEF DESCRIPTION OF THE DRAWINGS

Further details of the invention are disclosed in the following detailed description and the accompanying drawings in which preferred embodiments of the invention are illustrated by way of example. In the drawings.

DETAILED DESCRIPTION OF PREFERRED EMBODIMENTS

Figure 1:
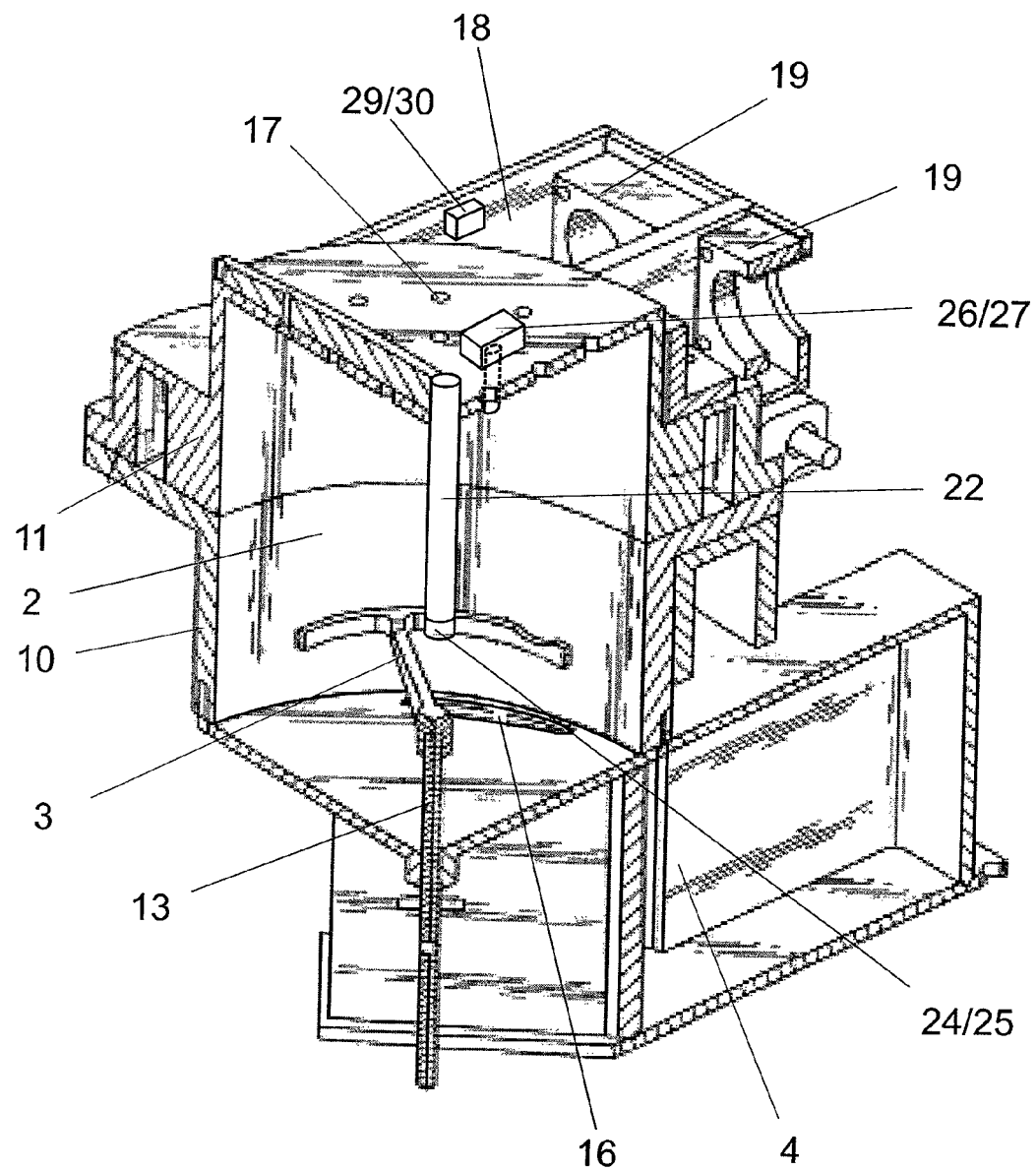
FIG. 1 is a perspective view of a test chamber without a covering hood, with a waveguide shown in section and outline.
Figure 2:
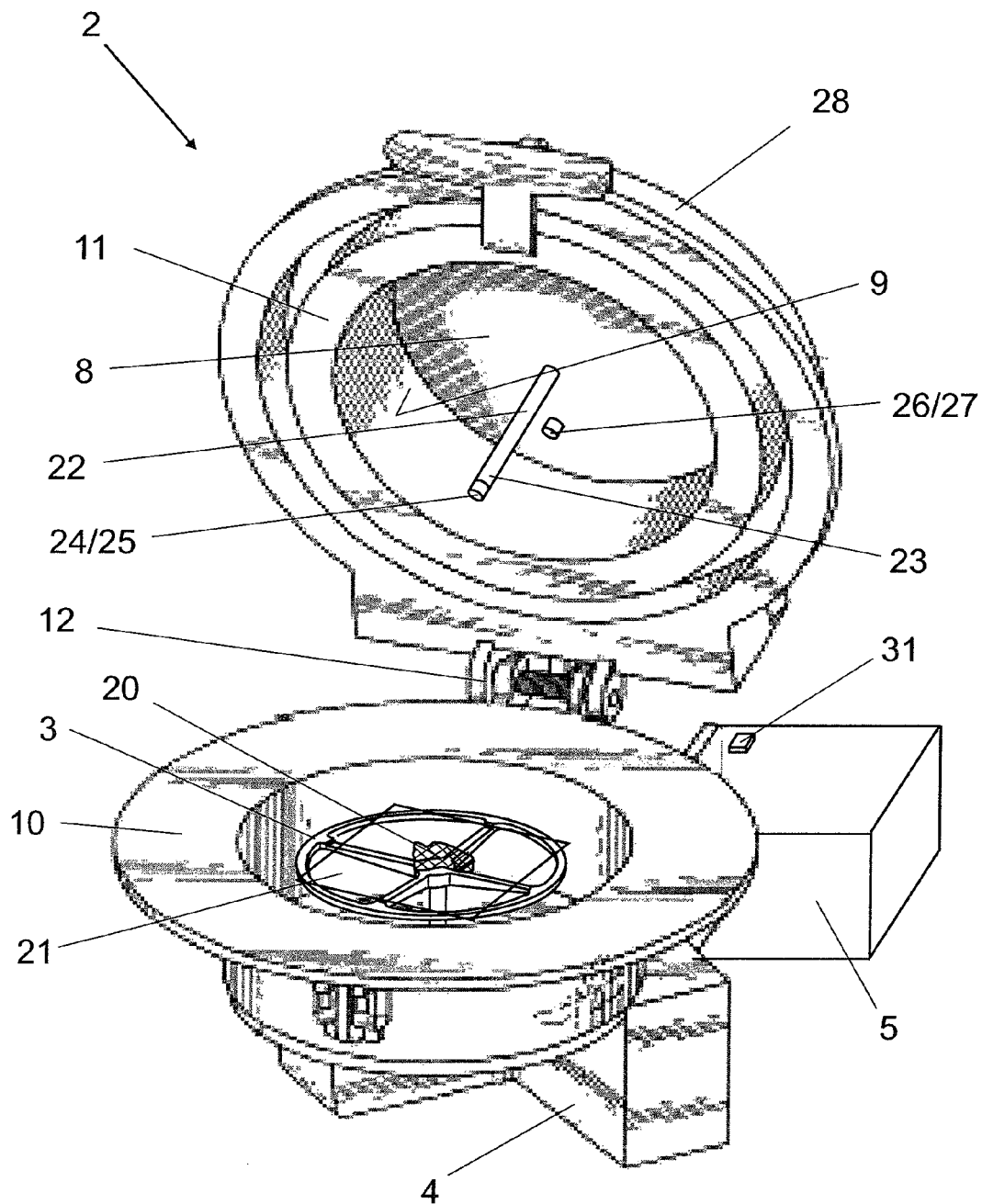
FIG. 2 is a perspective front view of an opened test chamber with a covering hood, a waveguide and a magnetron.
Figure 3:
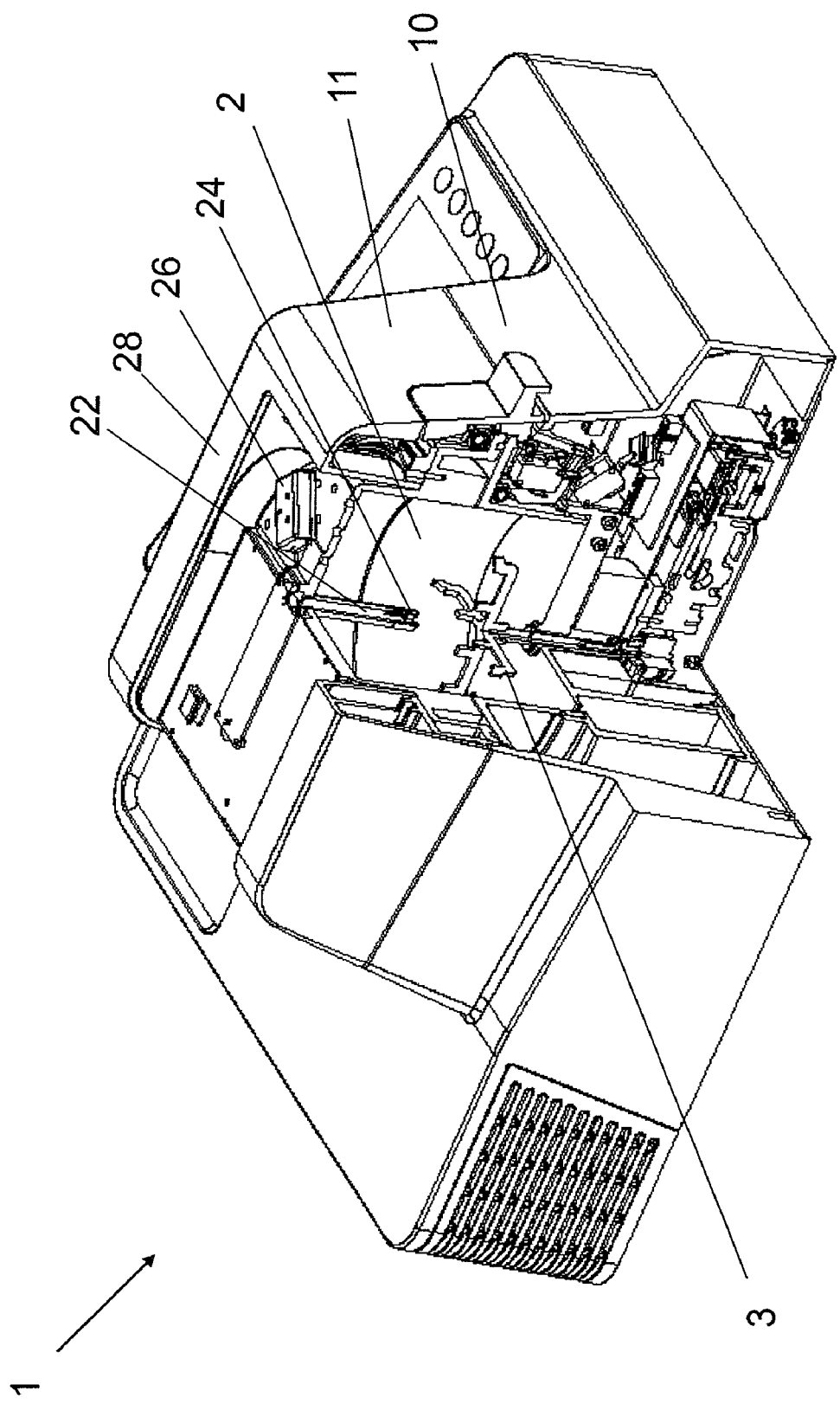
FIG. 3 is a partially cut-away perspective front view with an upwardly open cover and a further device for thermogravimetric material moisture determination.
Figure 4:
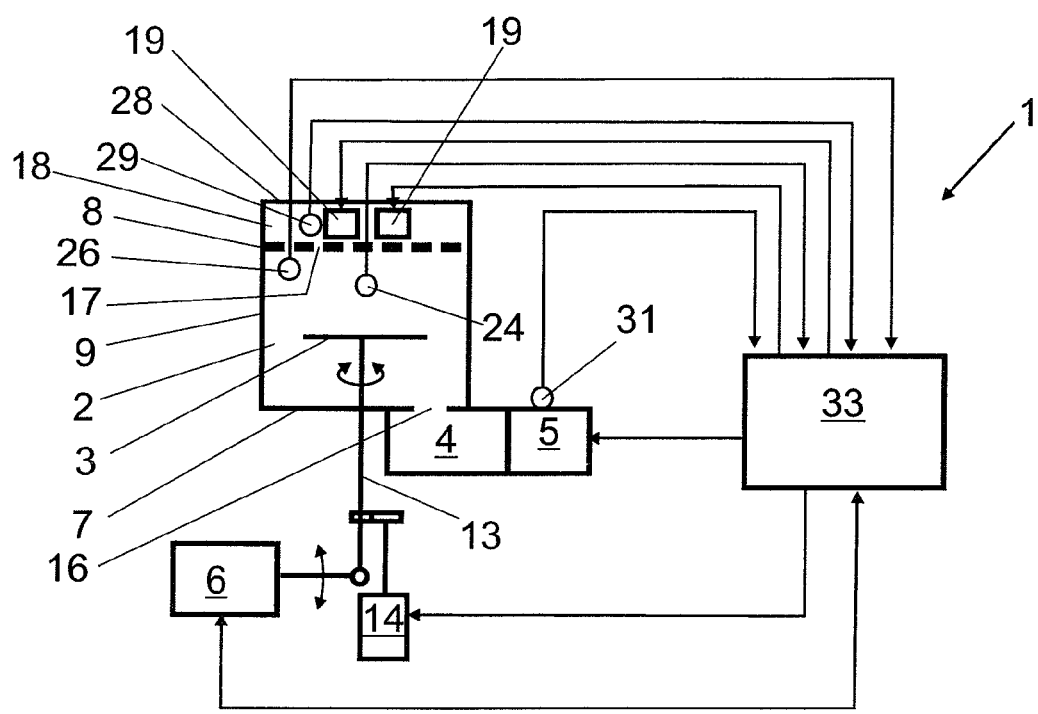
FIG. 4 shows a block circuit diagram of the device of FIG. 3.

FIGS. 1-4 show a device 1 for determining material moisture by thermogravimetry, which includes a test chamber 2 with a sample carrier 3, a waveguide 4, a magnetron 5 and a weighing module 6.

The test chamber 2 is delimited in the vertical direction at the bottom by a chamber base 7 and in the vertical direction at the top by a chamber cover 8. Laterally, the test chamber 2 is delimited by a cylindrical wall 9. The test chamber 2 is separated in the vertical direction into a lower portion 10 and an upper portion 11, wherein, for placement of samples into the test chamber 2, the upper portion 11 can be folded upwardly via a hinge 12.

The sample carrier 3 is arranged in the lower portion 10 and is in operative connection with the weighing module 6 via a vertical rotary axis 13 which extends through the chamber base 7. The sample carrier 3 is rotatable by means of an electric motor 14 via the rotation axis 13. The chamber base 7 is connected to the waveguide 4 which is configured Y-shaped. The microwaves generated by the magnetron 5 are supplied via the waveguide 4 through portals 16 arranged in the base of the test chamber 2. In the test chamber 2, the microwaves form a microwave field which heats a sample 20 or the material to be investigated after having been placed on the sample carrier 3. As a result, the moisture present in the sample 20 emerges as the result of a desiccation process.

Apertures 17 which open into one or more exhaust air channels 18 are formed in the chamber cover 8, via which channels 18 the moisture escaping from the sample 20 is drawn off by fans 19. In order to concentrate the microwave field onto the sample 20 which is placed, for example, on a glass plate 21 mounted on the sample carrier 3 or on a carrier made from another microwave-resistant material, a tuning rod 22 which is arranged with the free end 23 thereof facing away from the chamber cover 8 is arranged at the chamber cover 8 centrally above the sample carrier 3 or the sample 20. Arranged at the free end 23 is a sensor 24 which is configured, for example, as a no-contact temperature sensor 25, and in this example, an infrared sensor. Arranged in the test chamber 2 at the chamber cover 8 is a second sensor 26 which is configured, for example, as a microwave sensor 27.

Arranged in the exhaust air channel 18 which is formed between the chamber cover 8 and a covering 28 is a further sensor 29 which is configured, for example, as an air moisture sensor 30. A further sensor 31 which is configured as a temperature sensor 32 is also arranged at the magnetron 5.

The monitored values determined by the sensors 24, 26, 29, 31 are transmitted to a computer and control unit 33 which is configured as a microprocessor and which monitors and controls the whole measuring procedure and calculates the moisture of the sample or the material moisture.

The above description of preferred embodiments has been given by way of example. From the disclosure given, those skilled in the art will not only understand the present invention and its attendant advantages, but will also find apparent various changes and modifications to the structures and methods disclosed. The applicant seeks, therefore, to cover all such changes and modifications as fall within the spirit and scope of the invention, as defined by the appended claims, and equivalents thereof.

What is claimed is:

1. A device for determining material moisture by thermogravimetry, comprising:
    a test chamber delimited by a chamber cover,
    a magnetron generating a microwave field
    a waveguide supplying the microwave field to the test chamber,
    a tuning rod arranged in the test chamber,
    a sample carrier in operative connection with a weighing module mounted upstream of the test chamber, and
    at least one sensor arranged in the test chamber,
    wherein the tuning rod is arranged at the chamber cover centrally above the sample carrier and wherein the sensor is arranged at a free end of the tuning rod distal from the chamber cover.

2. The device according to claim 1, wherein the sensor is configured as a microwave sensor, as an air moisture sensor or as a non-contacting temperature sensor.

3. The device according to claim 2, wherein a second sensor is arranged in the test chamber.

4. The device according to claim 3, wherein the second sensor is configured as a non-contacting temperature sensor or as a microwave sensor.

5. The device according to claim 2, wherein the sensor is a temperature sensor configured as an infrared sensor.

6. The device according to claim 1, wherein the waveguide is fixed, wherein the sample carrier is configured to rotate about a rotation axis via which the sample carrier is connected to the weighing module, and wherein exhaust air apertures are provided in the chamber cover, via which an exhaust air stream generated by at least one ventilator is conducted out of the test chamber.

7. The device according to claim 6, further comprising an air moisture sensor in the exhaust air stream.

8. The device according to claim 1, further comprising a temperature sensor at the magnetron.

* * * * *